United States Patent [19]
Bader

[11] Patent Number: 5,222,942
[45] Date of Patent: Jun. 29, 1993

[54] SYRINGE, SPECIFICALLY FOR USE IN MEDICINE

[76] Inventor: Mohandes Bader, Neumünster, Fed. Rep. of Germany

[21] Appl. No.: 585,138
[22] PCT Filed: Jan. 30, 1989
[86] PCT No.: PCT/EP89/00076
  § 371 Date: Oct. 3, 1990
  § 102(e) Date: Oct. 3, 1990
[87] PCT Pub. No.: WO89/09630
  PCT Pub. Date: Oct. 19, 1989

[30] Foreign Application Priority Data
  Apr. 8, 1988 [DE] Fed. Rep. of Germany ... 8804656[U]
  Aug. 18, 1988 [DE] Fed. Rep. of Germany ....... 3828127

[51] Int. Cl.⁵ .............................................. A61M 5/00
[52] U.S. Cl. ..................................... 604/110; 604/218
[58] Field of Search ............... 604/110, 187, 218, 220, 604/208, 209

[56] References Cited

U.S. PATENT DOCUMENTS

| | | | |
|---|---|---|---|
| 3,890,936 | 6/1975 | McInerney et al. | 237/8 R X |
| 4,731,068 | 3/1988 | Hesse | 604/218 X |
| 4,820,272 | 4/1989 | Palmer | 604/220 X |
| 4,854,381 | 8/1989 | Mikula | 237/55 X |
| 5,000,737 | 3/1991 | Free et al. | 604/110 |

Primary Examiner—John D. Yasko
Attorney, Agent, or Firm—Lorusso & Loud

[57] ABSTRACT

Syringe, specifically for use in medicine, comprising a cylinder provided with an opening at its front end, wherein a plunger is disposed for displacement whose plunger rod projects from the rear end of the cylinder, with provisions for fluid-tight attachment or insertion of a needle, specifically an injection needle or a similar aspiration and/or administration element at or into the opening formed at or in the front end of the cylinder. Locking means are associated with the plunger and/or the plunger rod, which may be used to administer the maximum volume of the syringe only once.

38 Claims, 11 Drawing Sheets

SYRINGE, SPECIFICALLY FOR USE IN MEDICINE

DESCRIPTION

The present invention relates to a syringe, specifically for use in medicine, in accordance with the characterizing clause of claim 1.

Such syringes are commonly known in biomedical engineering, e.g. from the British Patent GB-A-20 15 883 or the Australian Patent AU-A-16 859. The syringe according to the Patent GB-A-20 15 883 substantially corresponds to the design according to the German Patent DE-B-29 09 992. As a matter of fact, these known syringes are destined for a single application only, to which end the inner wall of the cylinder includes at least one annular groove or undercut disposed normal to the cylinder axis for latching engagement of at least one radially outwardly urged plunger element such that it can no longer be retracted upon completion of the injection, with the plunger having reached its extreme ejection position within the cylinder. In order to prevent a multiple use of this injection syringe it is therefore definitely required that the plunger be pushed into and latched in its extreme ejection position. With a skilled manipulation of the plunger rod a multiple use of the known syringe is easily possible. The user has merely to see to it that the plunger will not be pushed forward up to its foremost position. Such an attempt merely requires the disposition of an annular spacer around the plunger rod outside of the cylinder between the latter and the operating element provided at the free end of the plunger rod. Thus this known injection syringe does not guarantee either the prevention of multiple use. In view of the ever-increasing risk of an AIDS infection due to the multiple use of injection syringes, in particular in less developed countries, the known syringe structures are not appropriate.

In the design according to the Patent AU-A-16 859 the charged volume of the syringe can be administered only in pre-dosed portions. It is moreover not obvious from that document that this known design allows for an initial displacement for aspiration. The process of charging the cylinder of the syringe appears to be hardly realizable in practice and seems to be also extremely exposed to the risk of contamination. To this adds an extremely doubtful sealing between the plunger and the plunger rod of that known design so that there is the risk of contamination also through this seal. For these reasons the design according to the Patent AU-A-16 859 is not very suitable for application in practice. It was not accepted in medical practice either even though this design has been known already since 1934.

The present invention is now based on the problem of improving a syringe of the type described by way of introduction to the effect that once the syringe has been used a continued use thereof will be reliably precluded, and that in particular any manipulation to render the syringe re-usable again will be prevented.

This problem is solved by the characterizing features of patent claim 1. Preferred structural details of the inventive design are defined in the dependent claims.

The essential aspect of the present invention thus resides in the provision of separate locking means in the form of a stopping collar through which the plunger rod passes, with said stopping collar cooperating with the plunger rod in a way that the volume of the syringe can be administered only administered only once, even when the plunger rod will be displaced in several partial strokes. Due to the separation of plunger, plunger rod, on the one hand, and locking means, on the other hand, the sealing and contamination problems explained in the foregoing with relation to the design according to the document AU-A-166 859 will not occur.

The features defined in claim 12 and the following claims offer an improved safety in the prevention of multiple use. These features result in a destruction of the syringe function so that a multiple use of the syringe is precluded even with application of force.

The injection needle is preferably fixedly linked up with the syringe cylinder so that in this way, too, a multiple use of the injection needles will be rendered impossible.

Other features of the invention will be explained in more detail hereinbelow with reference to the example of the embodiments illustrated in the drawing wherein:

FIG. 2 is a longitudinal sectional view of the syringe according to FIG. 1 in its assembled condition prior to use, with the plunger being pushed in;

FIGS. 5a to 5l illustrate each a conceivable cross-sectional shape of the plunger rod for a syringe according to FIGS. 1 to 4;

FIG. 6 is a longitudinal sectional view of an enlarged detail of a stopping collar provided as locking means cooperating with the plunger rod

FIG. 12 is a schematic longitudinal sectional view of a further embodiment of an inventive syringe prior to use, with the plunger being pushed in;

FIG. 18 is a schematic longitudinal sectional view of a fifth embodiment of an inventive syringe prior to use, with the plunger being pushed in;

FIG. 19b is a top view of the locking member according to FIG. 19a;

FIG. 20b is a bottom view of the locking member according to FIG. 20a;

FIG. 21b is a bottom view of the locking member illustrated in FIG. 21a.

The syringe according to FIGS. 1 to 4 consists of a cylinder 2, a plunger rod 13, a stopping collar 19, a plunger 12 with two axially spaced circumferential seals 39 and a guide element 9 for the plunger rod. The cylinder has a radially projecting collar 4 at its rear opened section 3. A connector 6 with an axial opening 7 is formed at the front end 5 of the cylinder 2. An injection needle or cannula or a similar aspiration and/or administration element which is not illustrated in more detail is undetachably attached, in particular bonded, in that axial opening.

Figure 1:
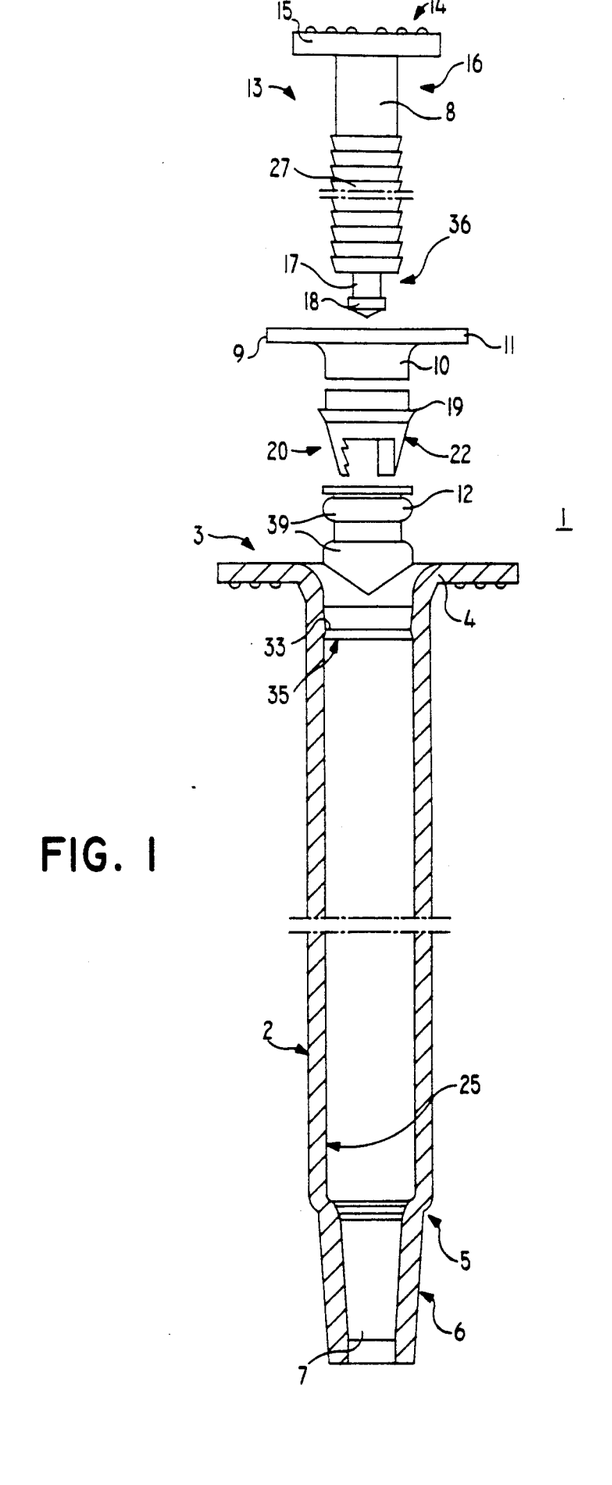
FIG. 1 shows a partially sectional exploded view of a first embodiment of a syringe.

The guide 9 consists of a guiding sleeve 10 with a flange 11 formed integrally therewith. The plunger rod 13 is guided inside the guiding sleeve 10. The flange 11 is supported on the collar 4 of the cylinder 2 when the guide 9 is mounted. The guide 9 may be connected to the cylinder 2 by bonding, welding or forceful pressing of the guiding sleeve 10 into the cylinder 2.

The plunger rod 13 consists of an elongate central part 8 carrying a manipulator 14 designed as an operating disk 15 at one end of the central part while at the other end 36 thereof a necked portion 17 is formed. The necking 17 is thus limited on one side by the central part having a wider diameter and on the other side by a bulge 18 at the end. The necking 17 is provided to hold the plunger 12, which consists of an elastomer and is pushed over the bulge 18 on the necked portion 17 when the syringe is assembled. A serration 27 is provided on the periphery of the central part 8 of the plunger rod 13. According to the more detailed illustration in FIG. 6 the teeth 28 are of a saw-tooth design and arrangement, with the tooth flanks 29 facing the bulge 18 or the plunger 12 being skew relative to the longitudinal axis 32 of the plunger rod while the tooth flanks 30 facing the manipulator 14 are orthogonal relative to the longitudinal axis 32 of the plunger rod. The serration 27 serves to bring the plunger rod 13 into operative mechanical engagement with the locking member 20 designed as stopping collar 19.

Figures 5A, 5B, 5C, 5D, 5E, 5F, 5G, 5H, 5I, 5K, 5L, 6:
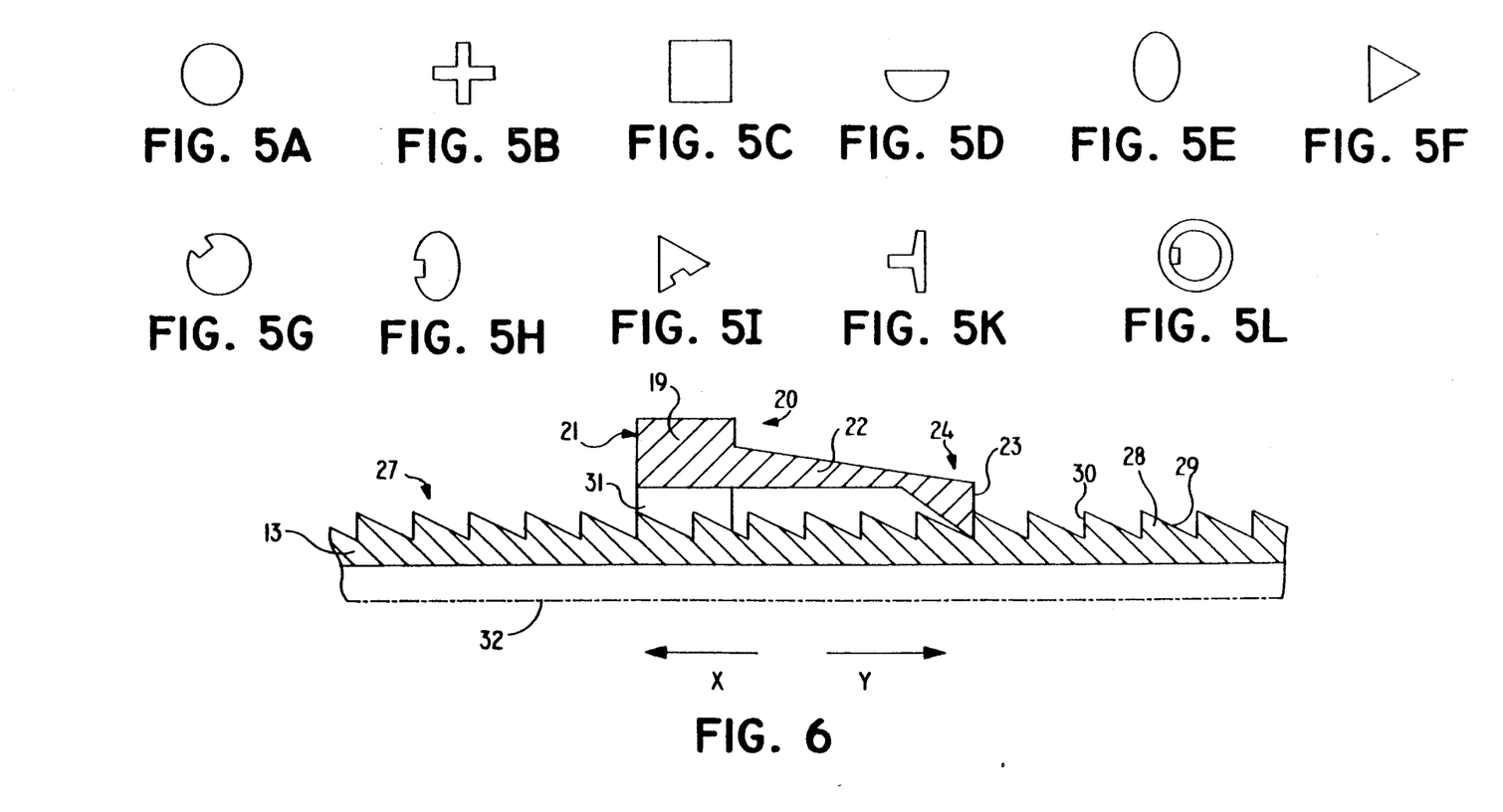
Figure 7:
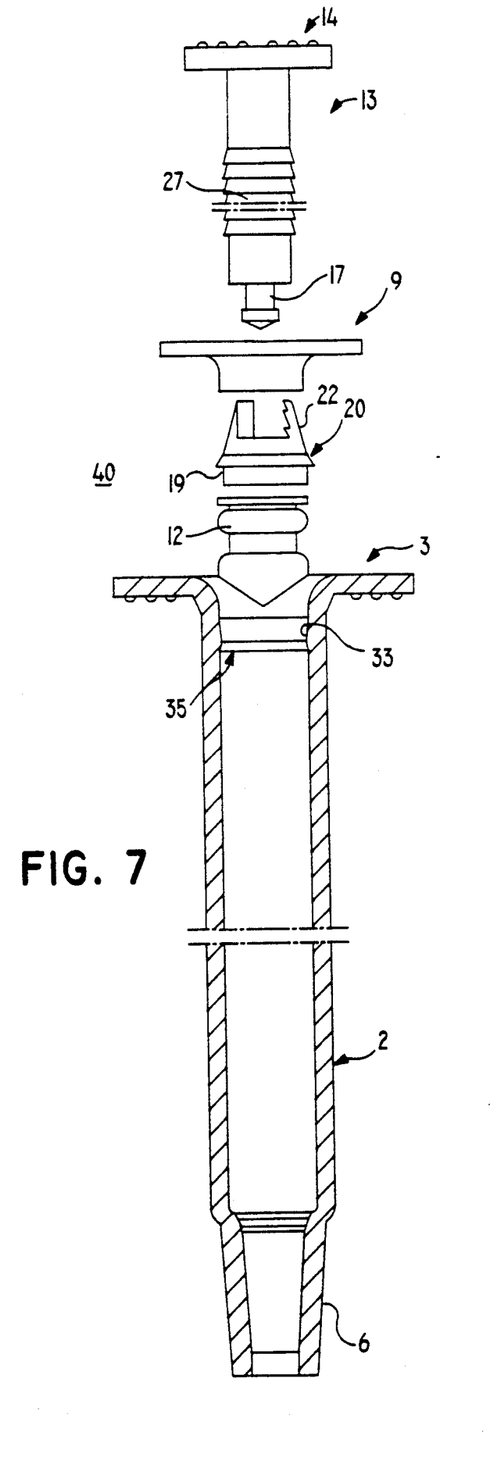
FIG. 7 is an exploded view according to FIG. 1 of a second embodiment of a syringe.
Figure 8:
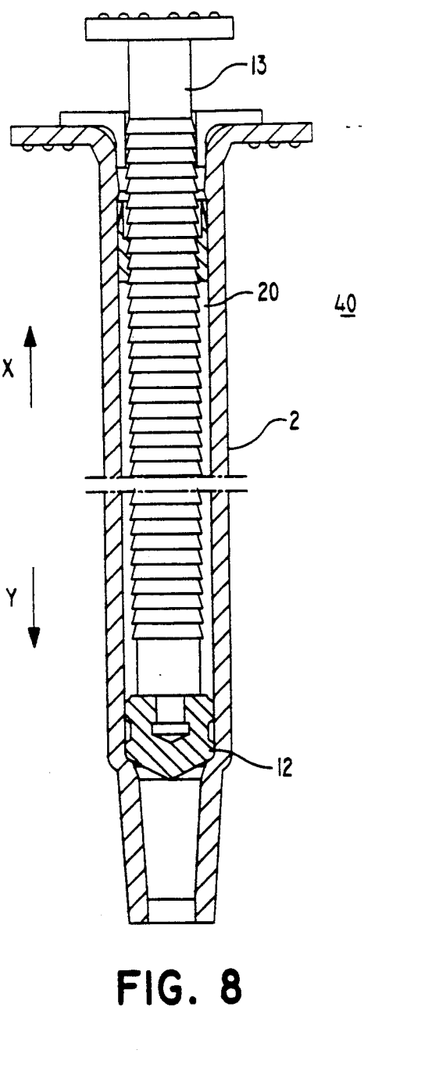
FIG. 8 is a longitudinal sectional view of the syringe according to FIG. 7 in its assembled position prior to use.
Figure 9:
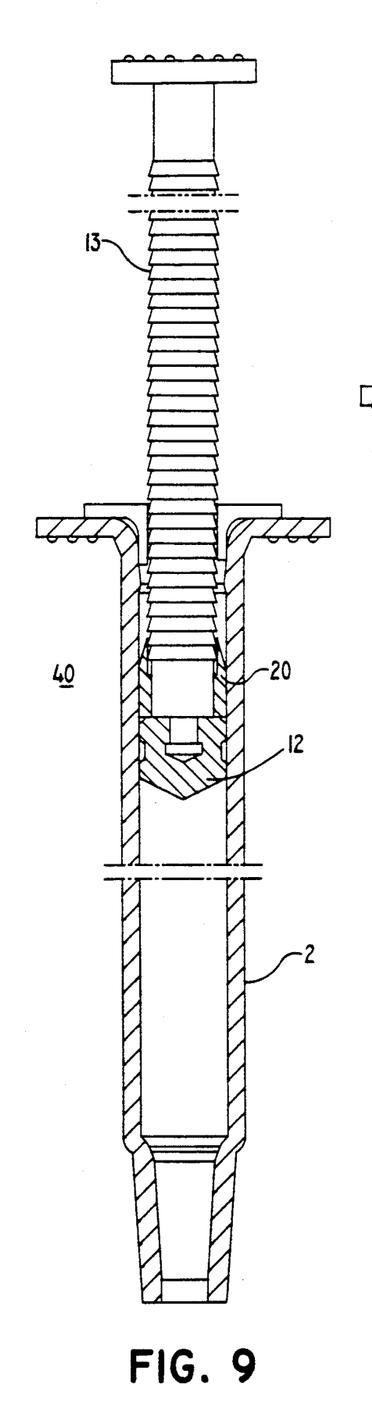
FIG. 9 is a longitudinal sectional view of the syringe according to FIG. 8 in a position at which an idle stroke begins.
Figure 10:
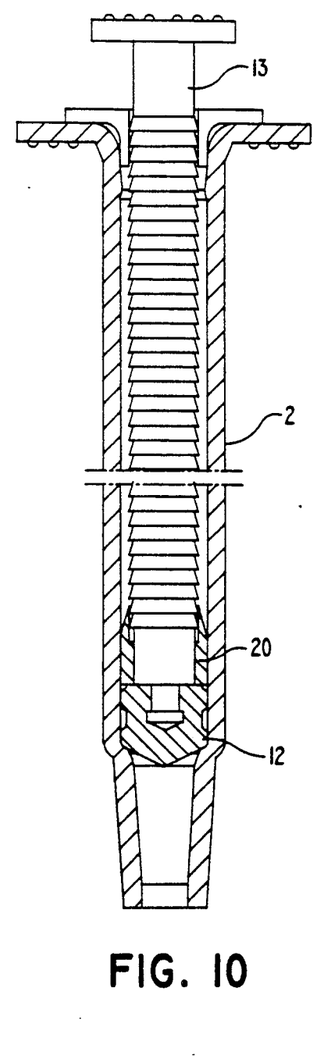
FIG. 10 is a longitudinal sectional view of the syringe according to FIG. 8 upon termination of the idle stroke, with the plunger rod being pushed into the cylinder.

Resilient check tongues 22 are formed at the stopping collar 19. The free end portions 24 of the tongues have the shape of inwardly oriented catches 23. These catches 23 are in operative engagement with the serration 27 of the plunger rod 13 of the assembled syringe. What is essential for the proper functioning of the stopping collar is the fact that its frictional resistance at the inner wall 25 of the cylinder 2 is greater than the clamping forces exerted onto the skew tooth flanks 29 by the catch 23 of the checking tongues 22.

Figure 2:
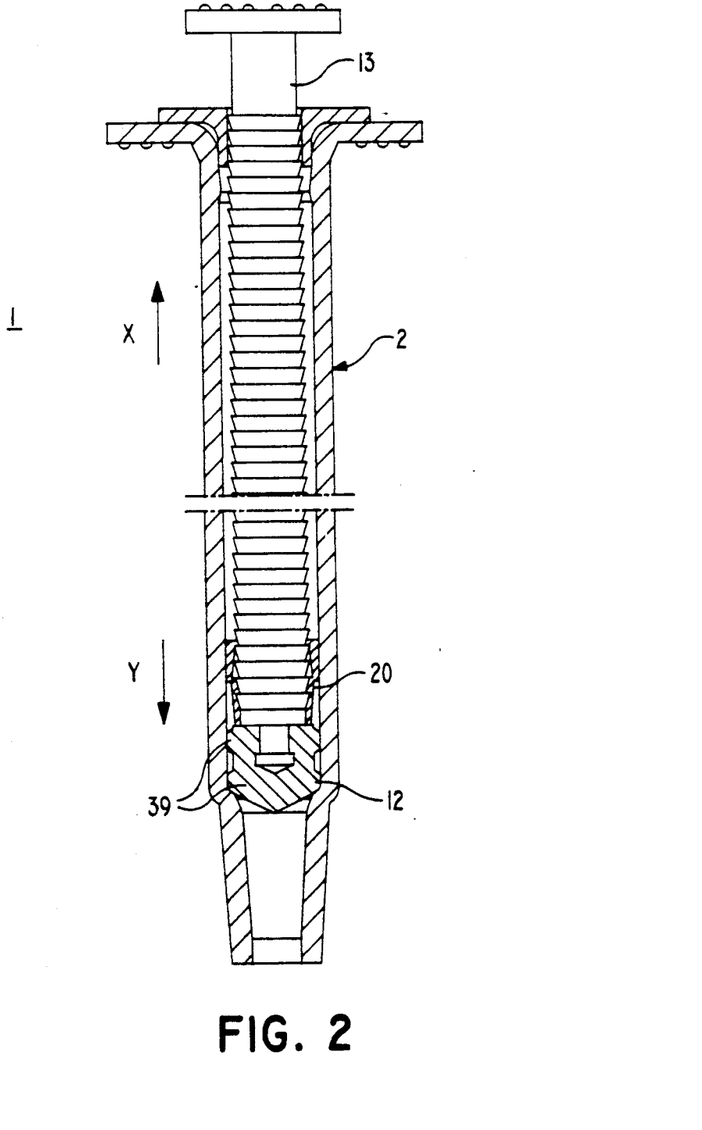

The syringe 1 is assembled as follows:

Initially the plunger 12 is pushed into the cylinder 2 until it reaches the area of the connector 6. Then the stopping collar 19 is pushed into the cylinder 2 until it bears against the plunger 12. Then the guide 9 is connected to the cylinder 2 whereupon the plunger rod 13 is inserted into the cylinder 2 and pressed against the plunger 12 until the latter slides over the bulge 18 and is fastened at the necking 17. In this position, which is illustrated in FIG. 2, the syringe 1 is ready for use.

Figure 3:
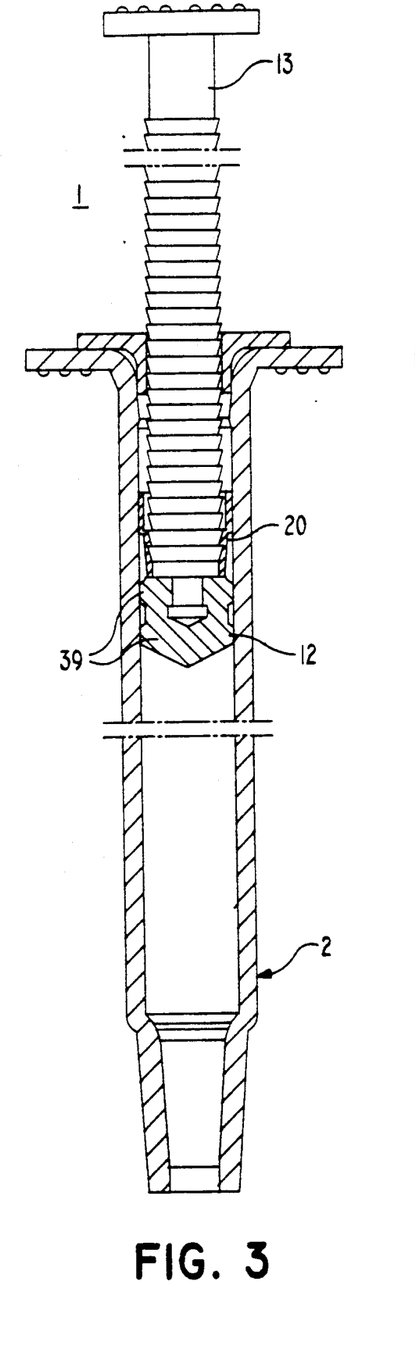
FIG. 3 is a longitudinal sectional view of the syringe according to FIG. 2, after a displacement for aspiration, with the plunger being withdrawn.
Figure 4:
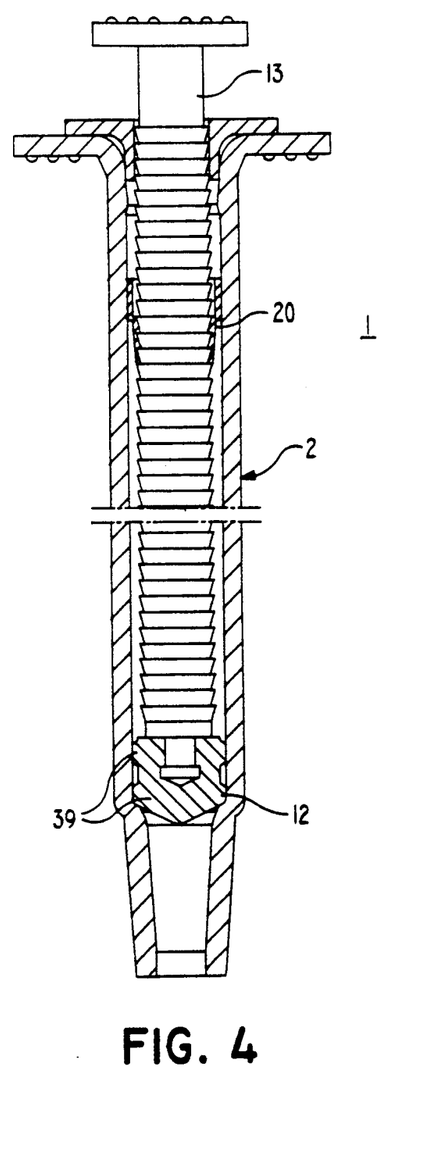
FIG. 4 is a longitudinal sectional view of the syringe according to FIG. 3 in the condition after an idle stroke, with the plunger being locked so as to prevent it from being withdrawn again.

When the plunger rod 13 is withdrawn from the cylinder 2, e.g. for taking a blood sample or charging the syringe with a medical solution, the catches 23 are locked in the serration 27 and bear against one of the tooth flanks 30. This action draws the stopping collar 19 with the plunger rod 13 in the direction of the opening section 3. A reversal of the plunger displacement into the ejection direction y, i.e. into the cylinder 2, unlatches the catches 22 while the stopping collar 19 remains fixed in its position in the cylinder 2 which it had assumed during the previous displacement of the plunger 12 or the plunger rod 13, respectively, in the direction x of displacement. Depending on the amount of this displacement the position in which the stopping collar 19 is clamped under the action of friction at the inner wall 25 of the cylinder 2 may be different. In the extreme end position the stopping collar bears against a reentrant edge 33 formed at the opening section 3 of the cylinder 2, which edge serves as anti-withdrawal stop and produces the effect that the syringe 1 cannot be dismantled without being destroyed (FIG. 3). During the aforementioned reversal of the plunger displacement into the direction y of ejection the catches 23 slide over the slanting tooth flanks 29 of the teeth 28 of the serration 27 without displacement of the stopping collar 19. With a repeated operation of the plunger 12 or the plunger rod 13 in the direction x of the displacement for aspiration the displacement of the stopping collar 19 in the direction towards the reentrant edge 33, in under the effect of the clamping force of the supported catches 23, may be continued only when the stopping collar 19 had previously been spaced from the edge. The plunger 12 or the plunger rod 13, respectively, can thus be withdrawn only once from the position ready for use, which is illustrated in FIG. 2, beyond the complete plunger stroke in the direction x of displacement into the extreme position illustrated in FIG. 3. In this position the cylinder 2 is filled with the maximum volume of the desired liquid, e.g. blood or a medical solution. The action of the stopping collar 19 produces the consequence that even though the plunger 12 or the plunger rod 13 may be pushed from the position shown in FIG. 3 into the cylinder 2 again a repeated withdrawal in the direction x of displacement is no longer be possible since this withdrawal is prevented by the catches 23 bearing against a tooth flank 30. Thus an idle stroke into a plunger position shown in FIG. 4 is still possible but a repeated stroke for aspiration is prevented. These provisions ensure that the syringe is usable only for an intended single application. The cylinder volume can be administered only once. And even a manipulation at the syringe will not allow for administration of a quantity exceeding the maximum cylinder volume.

A locking member 20 designed in the form of a stopping collar 19 may be used with the most different cross-sectional shapes of the plunger rod 13. FIGS. 5a to 5l illustrate conceivable cross-sectional shapes of the plunger rod 13 without claiming that this survey would be complete. These cross-sectional shapes merely require that the arrangement of the check tongues 22 with the catches 23 at the stopping collar 19 be appropriately matched with the cross-sectional shape of the plunger rod 13.

The syringe illustrated in FIGS. 7 to 10 corresponds to the aforedescribed syringe 1 in terms of its structural elements. In this case, however, the serration 27 is so designed that the tooth flanks 30 which are orthogonal relative to the longitudinal axis 32 of the plunger are oriented towards the lower end 36 of the plunger rod 13 while the tooth flanks 29 disposed at an oblique angle relative to the longitudinal axis 32 of the plunger are oriented towards the upper end 16 facing the manipulator 14. The syringe 40 is so assembled that the stopping collar 19 is located in the area of the upper reentrant edge 33 of the cylinder 2 when the syringe 40 is in its condition ready for use (FIG. 8), with the check tongues 22 being oriented towards the opening section 3 of the cylinder 2. In order to charge the cylinder 2 with the desired liquid the plunger rod 13 is withdrawn from the cylinder 2 in the direction x of displacement. The maximum aspiration stroke is limited in this embodiment by the plunger stopping at the end plane 21 of the stopping collar 19, which plane is opposite to the check tongues 22. For discharge of the cylinder 2 the plunger rod 13 is displaced in the direction y of ejection towards the connector 6 formed at the front end of the cylinder 2. During this movement the stopping collar 19 is displaced by the catches 23 bearing against a tooth flank 30 into the cylinder 2 as well. With a repeated reversal of the direction of displacement of the plunger 12 or the plunger rod 13 in the x direction the catches 23 produce an unlatching effect while the stopping collar 19 is fixedly clamped against the inner wall 25 of the cylinder 2. When the plunger 12 bears against the end plane 21 the necking 17 withdraws from the plunger 12 so that the plunger rod 13 may now be withdrawn from the cylinder 2 without having any function. The plunger rod can, however, not be introduced into the cylinder 2 again so as to re-establish the operability of the syringe, since the catches 23 prevent the necking 17 from being re-introduced into the plunger 12. Even if the serration 28 were smoothed, e.g. by polishing or lapping or similar methods, the syringe 40 is no longer suited for application since the clamped stopping collar 19 definitely prevents any displacement of the plunger 12 in any case, which means that the cylinder 2 can no longer be charged with a liquid. In distinction from the syringe 1, the syringe 40 presents an advantage in terms of operation insofar as there is no relative movement of the catches 23 on the serration 27 during the idle stroke. This results in the expedient fact that the operator has the feeling of safe manipulation which is essential particularly when an injection is administered.

The aforedescribed syringes 1 and 40 may be designed in a variety of sizes and in all types and models known.

It is also possible to design the locking member 20 in a way that a serration 27 may be dispensed with at the plunger rod 13. For instance, a resilient clamping tongue 41 of metal or the like may be integrally formed at the stopping collar 19, with the free end portion of this tongue showing towards the connector 6 in the assembled condition of syringe 1 and towards the reentrant edge 33 in the syringe 40; this tongue is caused, under the action of a spring, to rest on the plunger rod 13. The resilience of the clamping tongue 21 is so dimensioned that it is smaller than the frictional resistance produced by the stopping collar 19 at the inner wall 25 of the cylinder 2. When the plunger rod 13 is pushed into the cylinder a pressing force is created which urges the clamping tongue outwardly while the stopping collar 19 remains in its position. When the plunger or the plunger rod 13 is then withdrawn the stopping collar 19 is pushed in the direction towards the opening section 3 of the cylinder 2, at maximum up to the reentrant edge 33, in the manner described in the foregoing. Then the plunger 12 or the plunger rod 13 may be pushed into the cylinder 2 again but it can no longer be withdrawn.

It is also possible to simplify the structural design of the syringe 1 by omission of the guide element 9, which is expedient in particular with syringes of minor size. The same applies to the syringe 40.

Figure 12:
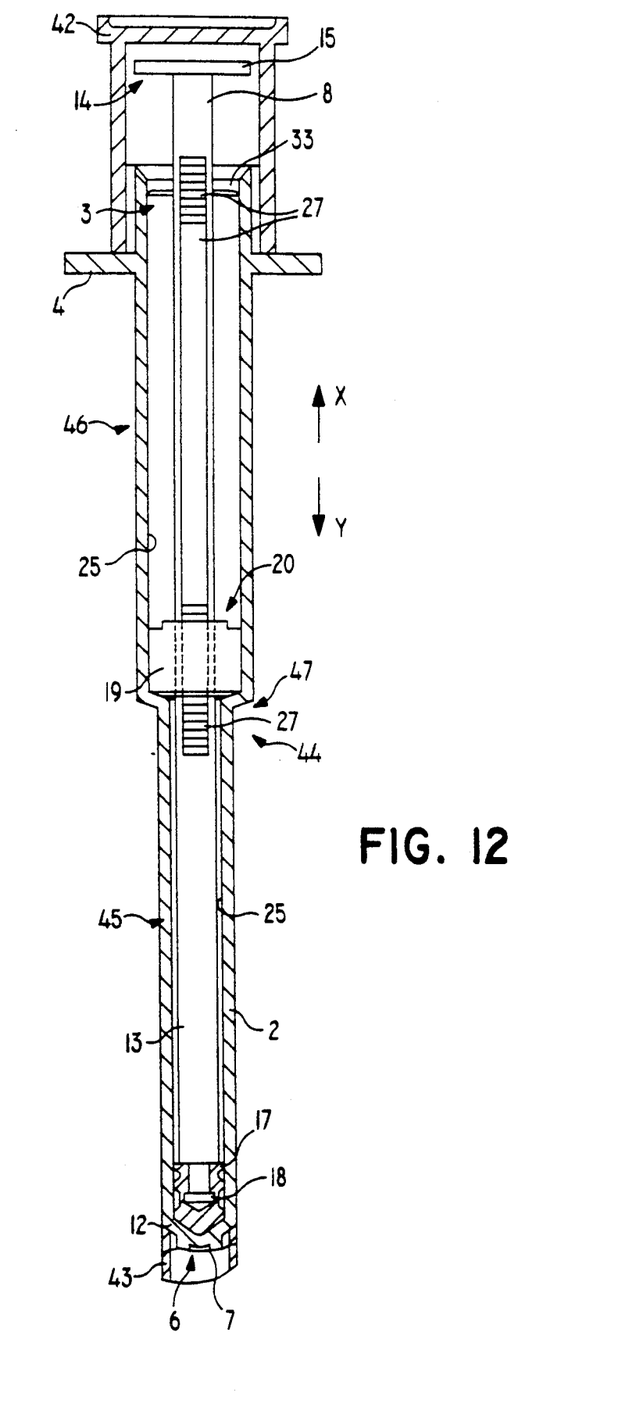

With reference to FIGS. 12 to 17 a further preferred embodiment of a syringe designed in accordance with the present invention will be described, with elements that have been described already in relation to the syringes 1 and 40 being identified by the same reference numerals applying thereto. Accordingly, the syringe 44 whose schematic longitudinal section is illustrated in FIG. 12 is composed of a cylinder 2 with a front, or in FIG. 12 a lower, cylinder section 45 and an upper section 46 (cf. FIG. 12) which faces the rear end of the syringe and has a diameter slightly greater than the diameter of the cylinder section 45. The circumferential step between the two cylinder sections 45, 46 is identified by reference numeral 47 in FIG. 12. In the lower cylinder section (cf. FIG. 12) the plunger 12 is supported for fluid-tight displacement relative to the inner wall 25 whilst in the upper cylinder section 46 the locking member 20, designed in the form of a stopping collar 19, is axial moved. Both cylinder sections have the same effective length. An upper guide element 9 has been omitted. In accordance with FIGS. 15 to 17 the plunger rod 13 consists of an elongate central part 8 provided with a manipulator 14 designed in the form of an operating disk 15 at one end 16 and with the necking 17 and bulge 18 at the other end, both in a manner similar to the embodiment illustrated in the preceding Figures. The plunger 12 presents a design equalling that of the aforedescribed embodiments and is fixed at the front end of the plunger rod 13. The embodiment provided with a separate guiding cylinder 46 for the stopping collar 19, which is not necessarily required to have a diameter greater than the diameter of the guiding cylinder 45 associated with the plunger 12, is distinguished from the aforedescribed embodiments by the advantage that the cylinder sliding surface 25 associated with the plunger 12 will not be damaged by mechanical action of the stopping collar 19 or its locking elements, respectively, which could give rise to leaks. This applies above all to cases where stopping collars 19 with metal clamping tongues are used which have an effect on the cylinder wall 25.

The embodiment having a widened guiding cylinder 46 is preferably used to accomodate locking members 20 with metal clamping tongues which act upon the cylinder wall with a locking effect.

In any case in use of the syringe the metal clamping tongues scrape along the cylinder wall, which results in the fact that plastic particles are scraped off the cylinder wall 25. When the cylinder sliding surface 25 is partly common to the locking member 20 and the plunger 12 these particles could pass between the locking member and the plunger, on the one hand, and the cylinder wall, on the other hand, into the medical medium to be administered and thus into the patient's bloodstream. The detrimental consequences are evident.

Figure 14:
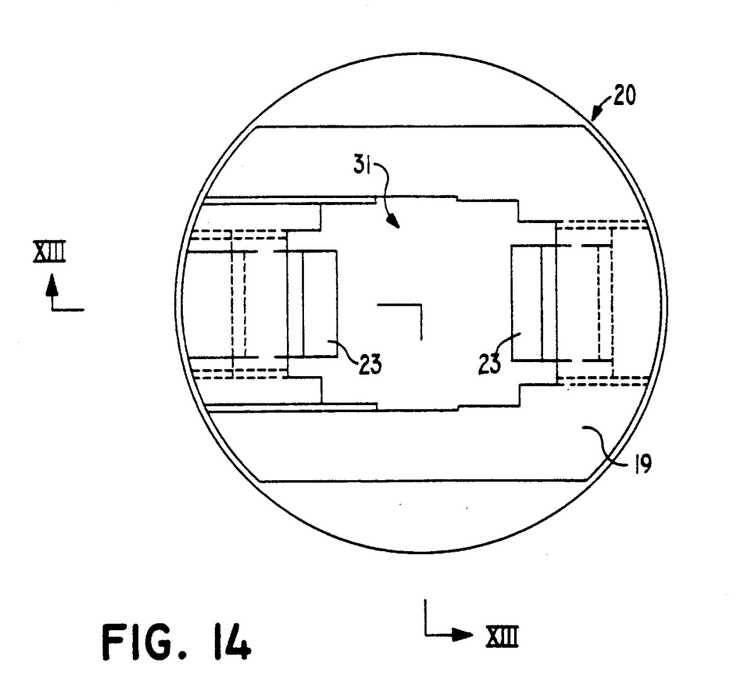
FIG. 14 is a top view of the stopping collar according to FIG. 13.
Figure 15:
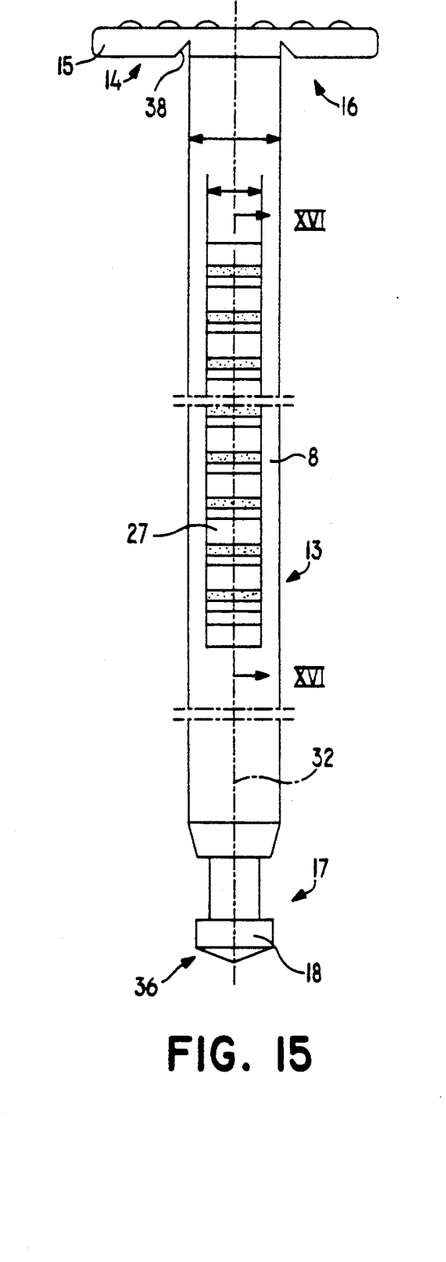
FIG. 15 is an enlarged side view of the plunger rod provided in the syringe according to FIG. 12.
Figure 16:
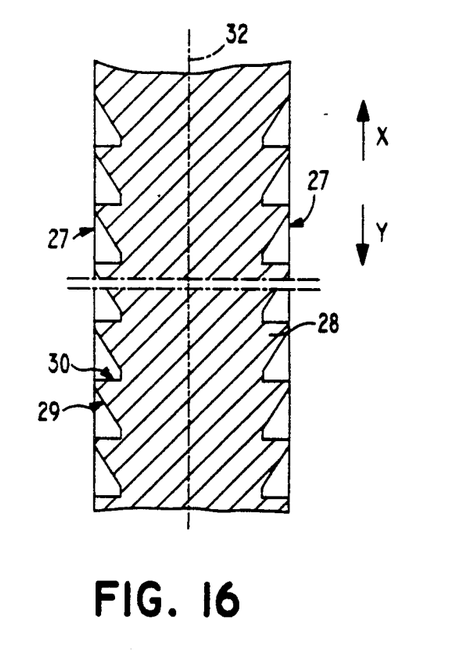
FIG. 16 is a sectional view of a portion of the plunger rod according to FIG. 15, taken along line XVI—XVI in FIG. 15.
Figure 17:
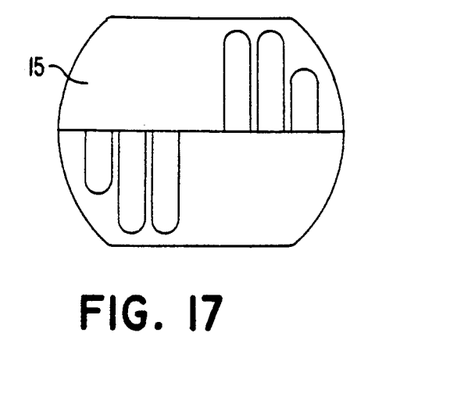
FIG. 17 is a top view of the plunger rod according to FIG. 15 or its operating disk, respectively.

As is shown in more detail in FIGS. 15 and 16 a diametrical serration 27 is formed along part of the overall length of the plunger rod 13, with the teeth 28 presenting a saw-tooth layout such that the tooth flanks facing the necking 17 slanting relative to the longitudinal axis 32 of the plunger rod and with the teeth flanks 30 facing the manipulator 14 being orthogonal relative to the longitudinal axis 32 of the plunger. It is by means of this serration 27 that the plunger rod 13 may be brought into an operative mechanical engagement with the locking member 20 designed in the form of a stopping collar 19 according to FIGS. 13 and 14.

Figure 13:
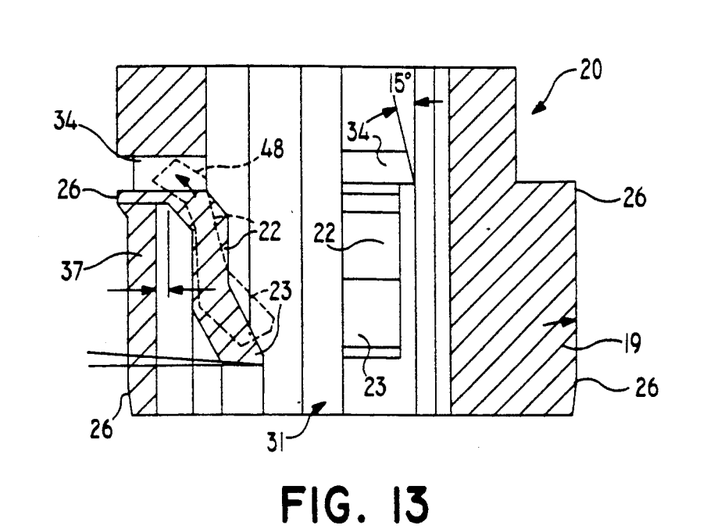
FIG. 13 is a sectional enlarged view of the stopping collar associated with the syringe according to FIG. 12.

According to FIGS. 13 and 14, diametrically opposing resilient check tongues 22 are formed at the stopping collar 19 which is supported for displacement in the upper cylinder section 46. The free end portions of these tongues have a design resembling that of the embodiment illustrated in FIGS. 1 to 6, i.e. they have the shape of inwardly oriented catches 23. These catches 23 are operatively engaged with the diametrically disposed serration 27 of the plunger rod 13 when the syringe is assembled. It is essential for the proper operation of the stopping collar 19 that its frictional resistance at the inner wall 25 of the upper cylinder section 46, which is shown in FIG. 12, is greater than the clamping forces exerted by the catches 23 of the check tongues 22 on the slanting tooth flanks 29. Separate prop ring projections 26 may be integrally formed at the stopping collars 19 (cf. FIG. 13) in order to increase the required frictional resistance between the stopping collar 19 and the inner wall or the cylinder sliding surface 25. The syringe 44 is assembled in a way similar to the assembly of the syringe 1, specifically as is described below:

First, the plunger 12 is pushed into the cylinder 2, specifically in the cylinder section 45, which is shown as the lower section in FIG. 12, up to the area of the bottom opening 7. Then the stopping collar 19 is pushed into the cylinder section 46, which is illustrated as the upper section in FIG. 12, until it bears against the circumferential step 47 between the upper and the lower cylinder sections. Then the plunger rod 27 is inserted into the cylinder 2, specifically through the locking element 19, and is pressed against the elastomer plunger 12 until the latter slides over the bulge 18 and is thus fastened at the necking 17. With this position, Which is illustrated in FIG. 12, the syringe 44 is ready for use. When the plunger 12 or the plunger rod 13, respectively, is withdrawn from the cylinder, e.g. to take in a medical solution, specifically a vaccine, the catches 23 come into locking engagement in the serration 27 and bear against one of the tooth flanks 30. Due to this effect the stopping collar 19 is caused to follow the plunger rod 13 in the direction towards the opening portion 3 of the cylinder 2, or upwardly in FIG. 12. When the plunger displacement is reversed into the direction of ejection y, i.e. into the cylinder 2, the catches 22 are unlocked while the stopping collar 19 remains fixed in its position due to the sufficiently great frictional locking action between the collar and the inner wall 25 of the cylinder section 46, i.e. the upper section in FIG. 12; this position had been reached during the previous displacement of the plunger 12 or the plunger rod 13 in the direction x of displacement. Depending on the amount of this displacement the position in which the stopping collar 19 is fixedly clamped against the inner wall of the cylinder section 46, i.e. the upper section in FIG. 12, under frictional action may be different. In the extreme position, i.e. the uppermost extreme position, the stopping collar 19 bears against the reentrant edge 33 formed at the opening portion 3 of the upper cylinder section 46, this edge having the effect of an anti-withdrawal stop and preventing the syringe from being dismantled without destruction. During the aforementioned reversal of the plunger displacement into the direction of ejection y, the catches 29 slide over the slantingly disposed tooth flanks 29 of the teeth 28 of the serration 27 without any displacement of the stopping collar 19. Upon a repeated operation of the plunger rod 13 in the direction x of displacement the displacement of the stopping collar 19 in the direction towards the reentrant edge 33, due to the clamping force of the supported catches 23, may be continued only if the collar had previously been spaced from that edge. The plunger 12 or the plunger rod 13, respectively, may thus be drawn out of the position ready for use, which is illustrated in FIG. 12, over the complete distance of plunger displacement in the direction of displacement x only once. It is accordingly also ensured that the maximum volume possible of the desired liquid may be ejected or administered for a single application only.

Since, in the aforedescribed embodiment according to FIGS. 1 to 6 for instance, it is fundamentally conceivable that under forceful action upon the plunger rod 13 in the direction of displacement the teeth 28 are ground and smoothed and thus lose their locking effect in cooperation with the catches 23, with the result that a multiple use of the syringe is possible, FIGS. 13 to 15 propose provisions preventing this possibility due to the fact that each of the locking elements in the form of the diametrically disposed check tongues 22, inclusive of the catches 23, is connected to the remaining part of the stopping collar 19 through a rated breaking point 37 in the form of a weaked portion in the material, with a radially outwardly extending clearance, here the passage 34, being disposed respectively directly above the rated breaking point; when the rated breaking point 37 breaks under excessively strong action onto the locking member 20 or the stopping collar 19 in the locking direction the locking member is urged into this clearance so as to establish an irreversible blocking position which is detrimental to the operation of the syringe, which is roughly indicated by the dotted line in FIG. 13 (cf. also arrow 48). In that position a practically unlockable clamping effect is achieved between the serration 27 at the plunger rod 13, on the one hand, and the stopping collar 19, on the other hand, by the "crossed" check tongues 22 inclusive of the catches 23. In this way an irreversible blocking of the plunger rod 13 is achieved. To facilitate the penetration of the broken-off check tongues 22 into the radial clearances 34 the check tongues 22 present a roughly S-shaped cross-section according to FIG. 13, with the catches 23 being respectively oriented towards the serration 27 of the plunger rod 13. FIG. 13 illustrates, by the way, a section taken through the stopping collar 19 along line XIII-XIII in FIG. 14, i.e. a sectional view in the diagonal direction.

In the embodiment described last additional or alternative provisions ensure a higher level of safety against a multiple use of the syringe; according to FIG. 15, these provisions consist in a connection of the operating disk 15 to the upper free end of the plunger rod 13 through a circumferential rated breaking line 38 in the form of a line along which the material is weakened. Under an excessively great load in the direction of the displacement for aspiration, i.e. when the plunger rod is locked for displacement in the direction x of displacement for aspiration, the operating disk 15 breaks off along the rated breaking line 38 and is detached from the plunger rod 13 so that operation of the plunger rod 13 in the direction of displacement x is no longer possible.

The aforementioned rated breaking line may also be provided in the upper area of the central part 8 of the plunger rod 13, specifically as a notch extending along the periphery of the central part 8 of the plunger rod 13. Under an excessively great load applied onto the plunger rod 13 the upper part of the plunger rod 13 would then break off the remaining part of the rod, with the rated breaking line being preferably located within the cylinder 2 in such a case so that not even by means of tools such as tongs, tweezers, or the like an operation of the plunger rod will become possible.

Special cap protectors 42, 43 are provided as means of protection in transport; one of these caps can be attached or plugged over the rear end of the syringe so as to cover the plunger rod, inclusive of the manipulator 14, which projects from the syringe, while the other cap may be attached or plugged over the front end of the syringe so as to cover the injection needle which is not illustrated in FIG. 12.

Figure 11:
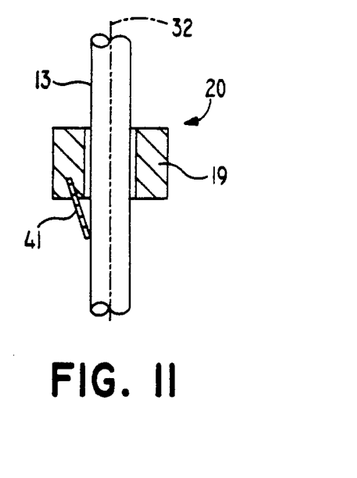
FIG. 11 is a partially sectional schematic side view of a third embodiment of a locking member.
Figure 18:
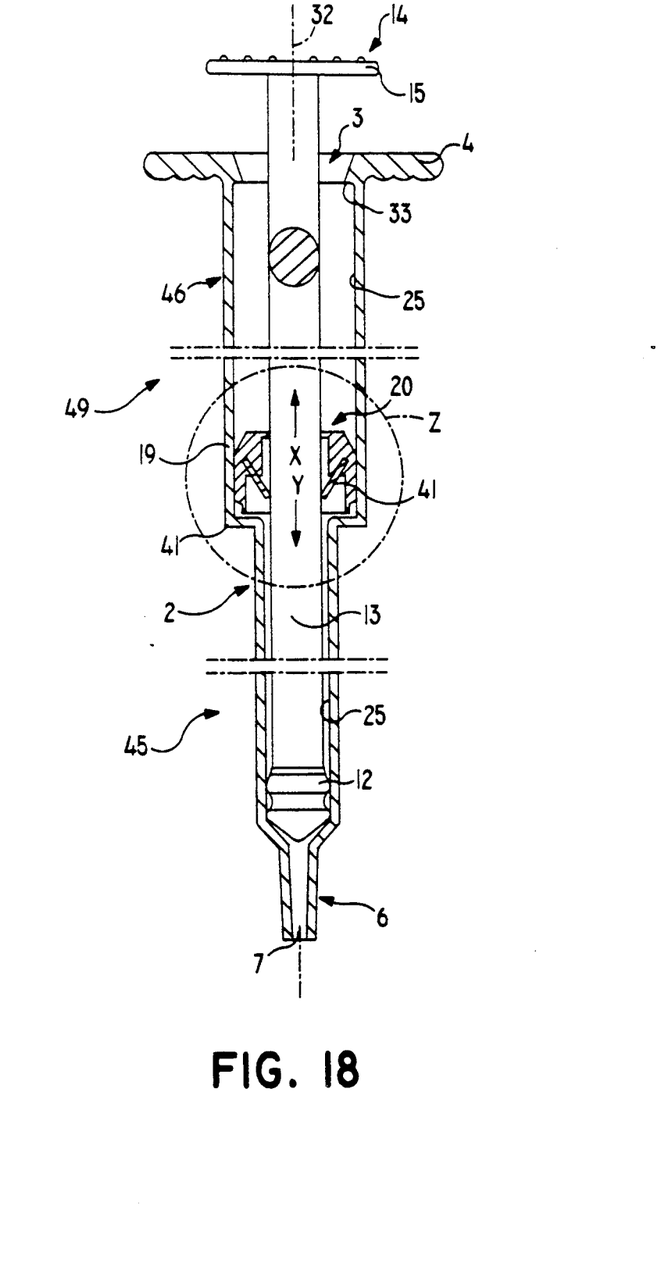

FIG. 18 is a schematic longitudinal section view of another embodiment of a syringe 49 designed in accordance with the present invention, which resembles the syringe according to FIG. 12 due to the provision of an upper cylinder section 46 and a lower cylinder section 45 of reduced diameter. What is of particular interest here is the locking member 20 which is provided with two or more diametrically disposed metal clamping tongues 41 in accordance with the embodiment of FIG. 11. The clamping tongues 41 are embedded by casting in the stopping collar 19 and produce a locking action upon the plunger rod 13 by their free ends, as has been described with reference to FIG. 11. With an odd number of clamping tongues they are preferably uniformly distributed along the periphery of the plunger rod which has a circular cross-section in the embodiment illustrated in FIG. 18.

Figure 19A:
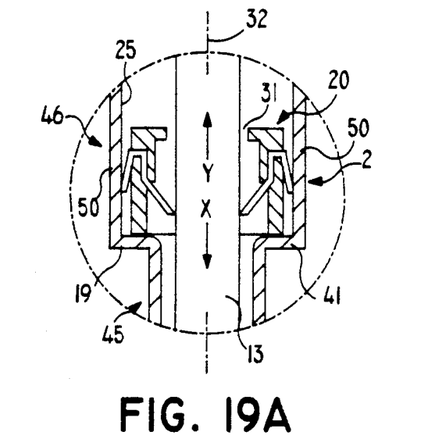
FIG. 19a is an enlarged longitudinal sectional view of the locking member for the embodiment according to FIG. 18.
Figure 19B:
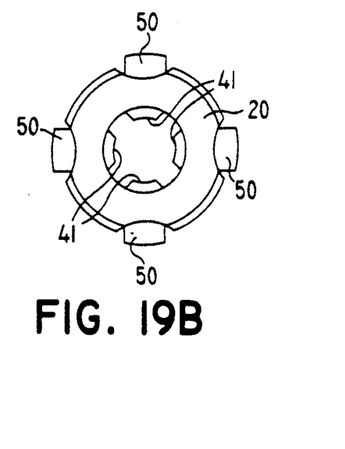

FIG. 19a is an enlarged longitudinal sectional view of the detail "Z" of FIG. 18 in a particularly clearly emphasizing illustration, i.e. the locking member 20 and its association with the syringe cylinder 2. In accordance therewith the locking element 20 is provided not only with clamping tongues 41 for cooperation with the plunger rod but also with clamping tongues 50 cooperating with the inner wall 25 of the cylinder section 46 of the syringe cylinder 2, which is associated with the locking member 20. The clamping tongues 50 substitute the aforedescribed frictional clamping action between the locking member 20 and the associated cylinder section or guiding cylinder 46, i.e. they provide for the fixed positioning of the locking member 20 after an intake stroke in the direction "x" of aspiration displacement. The clamping tongues 41 acting upon the plunger rod 13 thus lock the plunger rod 13 in the direction "x" of aspiration displacement while the outer clamping tongues 50 retain the locking member 20 in the direction "y" of ejection displacement at the inner wall 25 of the associated guiding cylinder or cylinder section 46. FIG. 19b illustrates a top view of the locking member 20 according to FIG. 19a.

Figure 20A:
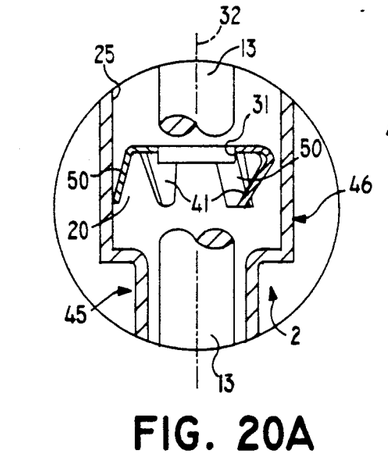
FIG. 20a corresponding to FIG. 19a, which illustrates an alternative embodiments of the locking member.
Figure 20B:
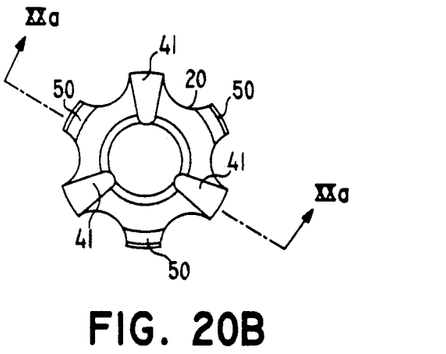

The embodiment shown in FIGS. 20a, 20b is identical with the design illustrated in FIGS. 19a, 19b in terms of its effect. Here merely a separate stopping collar 19 is omitted. The locking member 20 is an integrally punched and bent metal part. The clamping tongues 41 associated with the plunger rod 13 as well as the outer clamping tongues 50 associated with the inner wall 25 of the cylinder section 47 have been described already in terms of their effect or function with reference to FIGS. 19a, 19b. FIG. 20b is a bottom view of the locking member 20 shown in FIG. 20a while FIG. 20a is a transverse sectional view along line XXa—XXa in FIG. 20b and illustrates the locking member 20 of FIG. 20a.

Figure 21A:
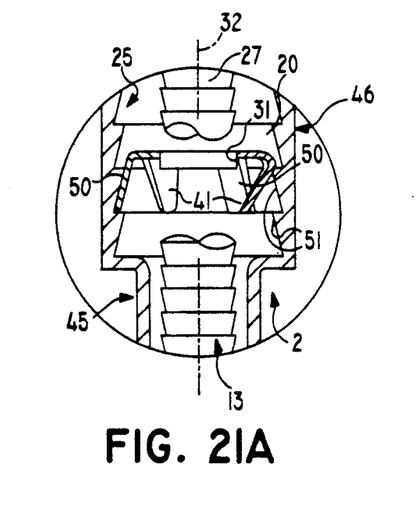
FIG. 21a is a view corresponding to FIGS. 19a or 20a, which illustrates another modified embodiment of the locking member.
Figure 21B:
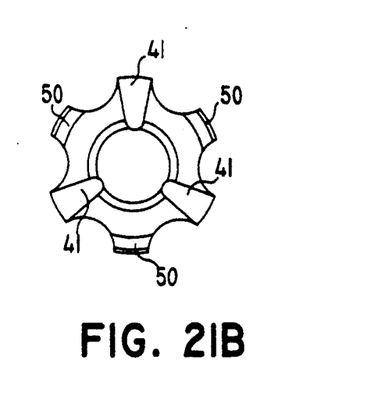

The embodiment according to FIGS. 21a, 21b is also of particular interest; it is characterized by an integral locking member 20 according to FIGS. 20a, 20b, however with the distinguishing provision that the locking member 20 of the embodiment shown in FIGS. 21a, 21b is preferably made of plastic material. To ensure yet the aforedescribed operational reliability in the x- and y-directions the inner and outer clamping tongues 41 and 50 cooperate with corresponding or complementary serrations at the plunger rod 13, on the one hand, and at the inner wall 25 of the cylinder section 46 of the syringe cylinder 2, on the other hand, which is associated with the locking member. The serration 27 on the plunger rod corresponds to the toothing provided according to FIGS. 1 to 4. The serration at the inner wall 25 of the cylinder section 46 of the syringe cylinder 2, which is associated with the locking member 20, is provided for cooperation with the outer clamping tongues 50 of the locking member 20 and is identified by the reference numeral 51 in FIG. 21a. It includes peripherally extending teeth having tooth flanks which extend orthogonally as well as at an oblique angle relative to the longitudinal axis 32 of the plunger or the syringe, respectively, with the first-mentioned tooth flanks facing the rear cylinder opening 3 and the latter tooth flanks facing the lower cylinder section 45 associated with the plunger 12. The serration 27 at the plunger rod 13 presents an equal design. Accordingly, the inner clamping tongues 41 cooperating with the serration 27 on the plunger rod lock the plunger 13 in the direction "x" of aspiration displacement while the outer clamping tongues 15 lock the locking member 20 in the direction "y" of ejection displacement against the inner wall 25 of the cylinder section 46 associated with the locking member 20. The embodiments of locking members 20, which are illustrated in FIGS. 19a to 21b, thus produce the same functions. Compared against the aforedescribed embodiments, the embodiment illustrated in FIGS. 21a, 21b, however, has the advantage that due to the positively locking cooperation between the locking member 20 and the plunger rod 13 or the inner wall 25 of the cylinder slip movements do not occur.

I claim:

1. Syringe, specifically for use in medicine, comprising a cylinder provided with an opening at its front end, wherein a plunger is disposed for displacement whose plunger rod projects from the rear end of the cylinder, with provisions for fluid-tight attachment or insertion of a needle, specifically an injection needle or a similar aspiration and/or administration element at or into said opening, characterized by locking means associated with said plunger and/or said plunger rod, which are provided for administration of the (maximum) syringe volume only once, wherein said locking means are provided with check elements interconnected through rated breaking points such that any attempt to overcome a frictional resistance associated therewith will cause them to break off, urging them into an irreversible blocked position detrimental to the function of the syringe.

2. Syringe according to claim 1, characterized in that a circumferential serration is formed on the envelope of said plunger rod.

3. Syringe according to claim 1, characterized in that said locking member is designed as a stopping collar whose outer wall bears against the inner wall (25) of said cylinder for displacement therealong and which includes an opening for guided displacement of said plunger rod as well as at least one stopping element in the form of a resilient clamping tongue of metal or a similar springy material whose free end portion is supported and resiliently biased, specifically under the action of spring pressure, on the envelope of the plunger rod at an oblique angle relative to the longitudinal axis of said plunger rod.

4. Syringe according to claim 3, characterized in that the frictional resistance of said stopping collar (19) at the inner wall of said cylinder is greater than the clamping force exerted by said (metal) clamping tongue onto said plunger rod.

5. Syring according to claim 1, characterized in that in the area of the rear opening of said cylinder a guide element is disposed whose guiding sleeve is inserted into said cylinder and passes through said plunger rod.

6. Syringe according to claim 1, characterized in that said check tongue(s), inclusive of said catch, serving as checking element or said clamping tongue serving as checking element is or are connected to the remaining portion of said locking member or said stopping collar, respectively, through a rated breaking location provided specifically in the form of a portion of weakened material.

7. Syringe according to claim 6, characterized in that with said rated breaking location is associated a radially outwardly extending clearance into said which said checking element or elements associated with said locking member may be urged so as to achieve an irreversible blocking position detrimental to the function of the syringe, whenever said rated breaking location breaks under excessively strong action onto said locking member in opposition to the locking effect produced by said member.

8. Syringe according to claim 1, characterized in that said plunger rod presents a rated breaking location in the area of its rear end or in the portion facing said manipulator, which breaking location is specifically designed in the form of an indentation extending along the periphery of said plunger rod, wherein said rated breaking location is preferably located within said cylinder with said plunger rod being pushed into the cylinder.

9. Syringe according to claim 1, characterized in that said locking member is an integral element having clamping tongues (respectively) cooperating with said plunger rod, on the one hand, and the inner wall of said syringe cylinder, on the other hand, such that during the aspiration displacement a locking action will be produced between said locking member, which is caused to follow, and said plunger rod and that during the ejection displacement a locking action will be produced between said locking member, which is fixed in its position in said cylinder, and the cylinder or the inner wall of the cylinder.

10. Syringe, specifically for use in medicine, comprising a cylinder provided with an opening at its front end, wherein a plunger is disposed for displacement whose plunger rod projects from the rear end of the cylinder, with provisions for fluid-tight attachment or insertion of a needle, specifically an injection needle or a similar aspiration and/or administration element at or into said opening, with locking means being associated with said plunger rod such that the volume of the syringe may be administered only once, characterized in that said locking means is a separate stopping collar through which said plunger rod passes for displacement so as to cause the stopping collar to follow only in the direction of the displacement for aspiration, such that during the ejection motion of said plunger rod said stopping collar will remain in the position into which it was caused to follow during the displacement for aspiration, without impeding said rod, specifically due to the frictional or positive locking effective in the direction of ejection between said stopping collar and the inner wall of said cylinder, on the one hand, while on the other hand, a repeated displacement for aspiration of the plunger rod is blocked due to engagement at said plunger rod.

11. Syringe according to claim 10, characterized in that said stopping collar includes at least one check element in the form of a checking tongue provided with a catch or in the form of a resilient clamping tongue made of metal or similar resilient material.

12. Syringe according to claim 10, characterized in that said plunger rod has a smooth envelope into which said resilient clamping tongue may penetrate so as to prevent a repeated aspiration displacement of the plunger rod.

13. Syringe according to claim 10, characterized in that said plunger rod is provided with a circumferential serration for mechanical engagement of said checking tongue(s) or clamping tongue such that a repeated aspiration displacement of said plunger rod will be prevented.

14. Syringe according to claim 13, characterized in that said serration presents a saw-toothing with teeth of equal tooth profile, with one tooth flank each of said teeth being disposed at an oblique angle relative to the longitudinal axis of the plunger rod and with the respective other tooth flank of said teeth being disposed orthogonally relative to said longitudinal axis of the plunger.

15. Syringe according to claim 10 characterized in that the movement of said locking member in the direction of the aspiration displacement (x) is limited by a stop in the area of the rear end of said cylinder.

16. Syringe according to claim 15, characterized in that in the area of the rear opening of said cylinder an anti-withdrawal stop is formed for said locking member, which serves at the same time as a stop to arrest the displacement of said locking member.

17. Syringe according to claim 16, characterized in that said anti-withdrawal stop is formed as a re-entrant edge of the inner wall of said cylinder, which reduces the area of unrestricted passage of said cylinder.

18. Syringe according to claim 16, characterized in that said anti-withdrawal stop is designed as a peripheral groove provided in the inner wall of said cylinder for latching engagement of a peripheral flange formed at said locking member.

19. Syringe according to claim 10, characterized in that in the area of the rear opening of said cylinder a guide element is disposed whose guiding sleeve is inserted into said cylinder and passes through said plunger rod.

20. Syringe according to claim 10, comprising a manipulator, specifically an operating disk, which is laterally salient at the free end of said plunger rod that projects from said cylinder, characterized in that said manipulator (operating disk) is connected to said plunger rod through a rated breaking line, specifically in the form of a line along which the material is weakened.

21. Syringe according to claim 10, characterized in that said locking means are provided with check elements interconnected through rated breaking points such that any attempt to overcome the check effect will cause them to break off, urging them into an irreversible blocked position detrimental to the function of the syringe.

22. Syringe according to claim 21, in that said check tongue(s), inclusive of said catch, serving as checking element or said clamping tongue serving as checking element is or are connected to the remaining portion of said locking member or said stopping collar, respectively, through a rated breaking location provided specifically in the form of a portion of weakened material.

23. Syringe according to claim 22, characterized in that with said rated breaking location is associated a radially outwardly extending clearance into which said checking element or element associated with said locking member may be urged so as to achieve an irreversible blocked position detrimental to the function of the syringe, whenever said rated breaking location breaks under excessively strong action onto said locking member in opposition to the locking effect produced by said member.

24. Syringe according to claim 10, characterized in that said plunger rod presents a rate breaking location in the area of its rear end or in its area facing said manipulator, which breaking location is specifically designed in the form of an indentation extending along the periphery of said plunger rod, wherein said rated breaking location is preferably located within said cylinder when said plunger rod is pushed into the cylinder.

25. Syringe according to claim 10, characterized in that said locking member is an integral element having clamping tongues cooperating with said plunger rod, on the one hand, and the inner wall of said syringe cylinder, on the other hand, such that during the aspiration displacement a locking action will be produced between said locking member, which is caused to follow, and said plunger rod, and that during the ejection displacement a locking action will be produced between said locking member, which is fixed in its position in said cylinder, and the cylinder or the inner wall of the cylinder.

26. Syringe according to claim 1, comprising a manipulator, specifically an operating disk, which is laterally salient at the free end of said plunger rod that projects from said cylinder, characterized in that said manipulator is connected to said plunger rod through a rated breaking line, specifically in the form of a line along which the material is weakened.

27. Syringe according to claim 1, characterized in that said locking means are disposed and operative inside said cylinder.

28. Syringe, in particular according to claim 1, characterized in that said needle specifically injection needle, is permanently fixed by bonding, welding or embedding in the cylinder material in the opening at the front end of said cylinder.

29. Syringe according to claim 1, characterized in that said locking means are mechanically operatively engaged with said plunger and said plunger rod such that said plunger, having performed a complete ejection stroke either in one stroke completely or gradually, is either blocked for a repeated aspiration displacement or irreversibly moved out of its operative engagement with said plunger rod by a repeated displacement for aspiration.

30. Syringe according to claim 1 characterized in that said locking means includes a locking member through which said plunger rod passes so as to cause the member to follow only in the direction of the aspiration displacement such that during the ejection displacement of said plunger rod the member will remain in the position into which it was caused to follow during the aspiration displacement, without impeding said rod, specifically due to the frictional or positive locking effective in the direction of ejection between said locking member and the inner wall of said cylinder.

31. Syringe according to claim 30, characterized in that the displacement of said locking member in the direction of the aspiration displacement is limited by a stop in the area of the rear end of said cylinder.

32. Syringe according the claims 31 characterized in that the area of the rear opening of said cylinder an anti-withdrawl stop is formed for said locking member which serves at the same time as a stop to arrest the displacement of said locking member.

33. Syringe according to claim 32, characterized in that said anti-withdrawl stop is formed as a re-entrant edge of the inner wall of said cylinder, which reduces the area of unrestricted passage of said cylinder.

34. Syringe, in particular according to claim 32, characterized in that said anti-withdrawl stop is designed as a peripheral groove provided in the inner wall of said cylinder for latching engagement of a peripheral flange formed at said locking member.

35. Syringe, according to claim 30, characterized in that said locking member is designed as a stopping collar whose outer wall bears against the inner wall of said cylinder for displacement therealong and which includes an opening for guided displacement of said plunger rod as well as at least one, preferably two, diametrically opposing locking elements, specifically in the form of resilient check tongues with one catch each, which tongues may be brought into mechanical engagement with a serration extending over part of the length of said plunger rod.

36. Syringe according to claim 35, characterized in that said serration presents a saw-toothing with teeth of equal tooth profile with one booth flank each of aid teeth being disposed at an oblique angle relative to the longitudinal axis of the plunger rod and with the respectively other tooth flank of said teeth being disposed orthogonally relative to said longitudinal axis of the plunger.

37. Syringe according to claim 30, characterized in that the frictional resistance developed by said stopping collar at the inner wall of said cylinder is greater than the clamping force exerted on said slanting tooth flanks by said catch of said at least one check tongue.

38. Syringe according to claim 30, characterized in that said serration is shaped in a rack-type form at a circumferential section of said plunger rod, in particular at diametrical sides of the latter.

* * * * *